United States Patent
Donnelly et al.

(10) Patent No.: US 12,324,615 B2
(45) Date of Patent: Jun. 10, 2025

(54) ASSESSMENT OF SOFT TISSUE TENSION IN HIP PROCEDURES

(71) Applicant: Mako Surgical Corp., Weston, FL (US)

(72) Inventors: William Donnelly, Chermside (AU); Matthew Thompson, Woodbridge, CT (US)

(73) Assignee: Mako Surgical Corp., Weston, FL (US)

( * ) Notice: Subject to any disclaimer, the term of this patent is extended or adjusted under 35 U.S.C. 154(b) by 318 days.

(21) Appl. No.: 17/980,793

(22) Filed: Nov. 4, 2022

(65) Prior Publication Data
US 2023/0141368 A1 May 11, 2023

Related U.S. Application Data

(60) Provisional application No. 63/276,292, filed on Nov. 5, 2021.

(51) Int. Cl.
*A61B 17/88* (2006.01)
*A61B 34/10* (2016.01)
*A61B 90/00* (2016.01)

(52) U.S. Cl.
CPC .......... *A61B 17/8869* (2013.01); *A61B 34/10* (2016.02); *A61B 90/37* (2016.02); *A61B 2034/105* (2016.02)

(58) Field of Classification Search
CPC .............................. A61B 17/8869; A61B 34/10
See application file for complete search history.

(56) References Cited

U.S. PATENT DOCUMENTS

| 4,517,969 A | 5/1985 | Halcomb, III et al. |
| 5,788,705 A | 8/1998 | Huddleston et al. |

(Continued)

FOREIGN PATENT DOCUMENTS

| JP | 2008536537 A | 9/2008 |
| WO | 2009067235 A1 | 5/2009 |

OTHER PUBLICATIONS

Loughenbury, F.,"Minimising leg length inequality after total hip replacement", Loughenbury Thesis, The University of Leeds, Leeds Musculoskeletal Biomedical Research Unit School of Medicine, Faculty of Medicine and Health (date deposited Aug. 30, 2018), (Part 1 of 2). Retrieved from White Rose eTheses Online https://etheses.whiterose.ac.uk/21329/ on Oct. 25, 2021.139 pgs.

(Continued)

*Primary Examiner* — Christian A Sevilla
(74) *Attorney, Agent, or Firm* — Lerner David LLP

(57) ABSTRACT

In one embodiment, the present disclosure relates to a method of evaluating soft tissue tension surrounding a hip of a patient using navigation and software to track positions of the femur and a pelvis of the patient in real time. The method begins with intra-operative reduction of a femoral implant into an acetabulum of a patient and retrieval of first coordinates of a femoral head center of the femoral implant when the femoral implant is in a reduced position. Performance of a shuck test follows where the femur is distracted relative to the acetabulum. Retrieval of second coordinates of the femoral head center occurs when the femoral implant is distracted from the acetabulum, and a difference between the first coordinates and the second coordinates in a coronal plane is used to determine a shuck length vector.

20 Claims, 9 Drawing Sheets

(56) References Cited

U.S. PATENT DOCUMENTS

| | | | |
|---|---|---|---|
| 7,458,989 B2 | 12/2008 | Banks et al. | |
| 7,725,162 B2 | 5/2010 | Malackowski et al. | |
| 8,007,448 B2 | 8/2011 | Moctezuma de la Barrera | |
| 8,992,542 B2* | 3/2015 | Hagag | A61F 2/36 606/130 |
| 9,017,335 B2 | 4/2015 | Stiehl | |
| 9,044,345 B2 | 6/2015 | Warkentine et al. | |
| 9,237,949 B2 | 1/2016 | Podolsky et al. | |
| 10,251,663 B2* | 4/2019 | Behzadi | A61B 17/142 |
| 11,432,828 B1* | 9/2022 | Lang | G16H 70/20 |
| 2007/0021644 A1 | 1/2007 | Woolson et al. | |
| 2014/0200621 A1 | 7/2014 | Malackowski et al. | |
| 2018/0325608 A1* | 11/2018 | Kang | A61B 17/1671 |
| 2020/0281742 A1* | 9/2020 | Wu | A61B 34/30 |

OTHER PUBLICATIONS

Loughenbury, F., "Minimising leg length inequality after total hip replacement", Loughenbury Thesis, The University of Leeds, Leeds Musculoskeletal Biomedical Research Unit School of Medicine, Faculty of Medicine and Health (date deposited Aug. 30, 2018), (Part 2 of 2). Retrieved from White Rose eTheses Online https://etheses.whiterose.ac.uk/21329/ on Oct. 25, 2021. 140 pgs.

Naito, M., et al., "Intraoperative limb length measurement in total hip arthroplasty", Springer-Verlag, International Orthopaedics (SICOT) (1999) 23, pp. 31-33.

Rossi, R., et al., "Soft Tissue Balancing in Primary Total Knee Arthroplasty", Edizioni Minerva Medica Torino (2012). 20 pgs.

Sathappan S., et al., "Effect of Anesthesia Type on Limb Length Discrepancy After Total Hip Arthroplasty", The Journal of Arthroplasty vol. 23 No. 2 (Feb. 2008). 8 pgs.

Tanino, H; Higa, et al., "Sensor-Instrumented Modular Head for Measuring Soft-Tissue Tension During Total Hip Arthroplasty", 55th Annual Meeting of the Orthopaedic Research Society (2009). 1 pg.

Loughenbury, F., et al., "Hip surgeons and leg length inequality after primary hip replacement,", Hip International (2019), vol. 29(1), pp. 102-108.

* cited by examiner

|  | Male | Female | Total |
|---|---|---|---|
| Number of Patients | 25 | 36 | 61 |
| Mean Age (range of age) | 63.14 | 60.44 | 62.03 |
|  | (39 - 77) | (34 - 77) | (34 - 77) |
| Mean BMI (range) | 28.48 | 24.82 | 27.21 |
|  | (21.15 - 39.27) | (18.90 - 31.70) | (18.90 - 39.27) |
| Side of Body | Left (15) | Left (8) | Left (23) |
|  | Right (21) | Right (17) | Right (38) |

FIG. 4

|  | Male | Female | Overall |
|---|---|---|---|
| Mean Pre-Op Hip Length compared to contralateral, mm (one standard deviation, mm) | -2.64 (5.21) | -0.4 (4.72) | -1.72 (5.10) |
| Mean Pre-Op Offset compared to contralateral, mm (one standard deviation, mm) | 1.81 (5.52) | 0.24 (4.74) | 1.16 (5.23) |
| Mean Reduced Hip Length compared to pre-op ipsilateral, mm (one standard deviation, mm) | 2.72 (4.72) | 3.2 (3.20) | 2.92 (4.14) |
| Mean Reduced Offset compared to pre-op ipsilateral, mm (one standard deviation, mm) | -2.17 (4.69) | -1.2 (4.69) | -1.77 (4.68) |
| Mean Reduced Hip Length compared to contralateral, mm (one standard deviation, mm) | 0.08 (4.66) | 2.8 (4.94) | 1.20 (4.93) |
| Mean Reduced Offset compared to contralateral, mm (one standard deviation, mm) | -0.36 (7.82) | -0.96 (6.59) | -0.61 (7.29) |

FIG. 5

| Shuck Test | Male | Female | Overall |
|---|---|---|---|
| Mean Hip Length Shuck Distance, mm (one standard deviation, mm) | 7.73 (4.41) | 6.36 (3.05) | 7.17 (3.94) |
| Mean Hip Offset Shuck Distance, mm (one standard deviation, mm) | 7.06 (4.52) | 5.52 (3.25) | 6.43 (4.09) |
| Mean Shuck Length Vector magnitude, mm (one standard deviation, mm) | 10.98 (5.34) | 8.77 (3.71) | 10.07 (4.83) |
| Mean Shuck Length Vector direction, angle in degrees relative to horizontal when patient in lateral decubitus position (one standard deviation, degrees) | 41.94 (17.11) | 40.75 (14.98) | 41.45 (16.15) |

FIG. 6

ASSESSMENT OF SOFT TISSUE TENSION IN HIP PROCEDURES

CROSS-REFERENCE TO RELATED APPLICATION

This application claims the benefit of the filing date of U.S. Provisional Patent Application No. 63/276,292, filed Nov. 5, 2021, the disclosure of which is hereby incorporated by reference herein in its entirety.

BACKGROUND OF THE DISCLOSURE

Total hip arthroplasty procedures have arguably been one of the most successful types of procedures in orthopedics. However, favorable results have depended on accurate implant component positioning and restoration of pre-disease or pre-injury biomechanics in the hip, including restoration of the center of rotation, leg length and offset. Additionally, in terms of the consideration of soft tissue in the hip joint, there have been limited developments in technology and techniques to provide assessments intra-operatively. Although a number of subjective tests have been used intraoperatively to give the surgeon some indication of tissue tension source such as the "shuck" and "kick" tests, these tests only give the surgeon a "feel" for tissue tension and do not provide quantitative information as to hip stability or soft tissue tension. Put another way, the results of the shuck test and other similar tests have been subjective due to their ultimate reliance on surgeon judgment. In this manner, the shuck test has not provided a reliable and objective measure of soft tissue tension in the hip.

Accordingly, there is a need for a dependable approach to intra-operatively measure soft tissue tension in the hip in order to improve soft tissue balance in post-operative hip joints.

BRIEF SUMMARY OF THE DISCLOSURE

In one aspect, the present disclosure relates to a method of intra-operatively evaluating soft tissue tension in a hip joint to determine whether changes should be made to one or more of the hip offset and hip length through adjustment of a reduced position of an implant positioned in the femur or replacement of the implant with another of a different size or geometry. To make such evaluation, a "digital output shuck test" is performed. The shuck test may have digital output because, among other reasons, the results are measured in an objective manner, as will be described throughout this disclosure. The digital output shuck test is also referred to throughout the present disclosure as simply the "shuck test", "intra-operative test" or "test" when referenced as part of embodiments of the present disclosure. When the shuck test is performed, locations of anatomy on a femur and a pelvis of the patient are already registered through a navigation system so that their real-time positions may be monitored. Optionally, locations on a femoral implant may also be registered. In this manner, when the femoral head of the implant is distracted to a desired position relative to the acetabulum, a change in offset, a change in leg length, and a direction of the distraction are all recorded through software linked to the navigation system. From this information, a shuck length vector may be derived that indicates an overall magnitude of the distraction and a direction of the distraction relative to an anatomic coordinate system defined by pelvic coordinate system with its origin at the center of the acetabulum. In a variation, a directional soft-tissue restraint limit may be determined and used as an additional guide to evaluate whether the direction of the shuck length vector is adequate to use as a reference. With reference to the shuck length vector, the direction may first be evaluated to assess whether the shuck test was performed correctly by evaluating how close the direction of distraction is to the center axis of the acetabulum or intended direction, or by evaluating whether the direction and position falls within the directional soft-tissue restraint limit. If the direction is acceptable, then the magnitude may be assessed. If a magnitude of the shuck length vector is outside of a prescribed range, e.g., less than 5 mm or greater than 15 mm, a surgeon should consider an adjustment of the implant that would bring the soft tissue tension closer to or into the prescribed range. For example, when a magnitude of the shuck length vector is less than 5 mm, the implant may be adjusted to obtain a hip offset and hip length that will reduce soft tissue tension. And, when a magnitude of the vector is greater than 15 mm, the implant may be adjusted to obtain a hip offset and hip length that will increase soft tissue tension.

One advantage of the present disclosure is the quantification of the magnitude of the shuck test. Building on this objective measure, methods are advantageously established to describe the variability of soft tissue balance in a patient population and to assess the extent to which soft tissue tension correlates to leg offset or leg length changes or discrepancies. With these relationships, the present disclosure provides a way to predictably evaluate existing hip offset and hip length and whether planned post-operative hip components including leg length and offset should be revised based on measured soft tissue tension identified through the described shuck test. One of the ways the present disclosure may guide a surgeon is through a proposed safe range of shuck length magnitude indicative of adequate soft tissue tension such that when a measured shuck length is outside of the safe range, adjustment of the hip implant may be advisable. Yet another advantage of the present disclosure is the identification of anatomical measures that have the strongest correlation with the magnitude of the shuck length vector. These advantages are realized in part through the use of robotics and associated navigation systems.

In one aspect, the present disclosure relates to a method of evaluating soft tissue tension surrounding a hip of a patient. In one embodiment, the method involves using navigation and software to track positions of the femur and a pelvis of the patient in real time and also involves implanting a femoral implant or a trial in the femur. The method proceeds with steps including: intra-operatively reducing a femoral implant or a trial into an acetabulum of a patient; retrieving first coordinates of a femoral head center of the femoral implant or trial when the femoral implant or trial is in a reduced position; performing an intra-operative test to bring soft tissue of the patient into tension that includes gripping a neck of the femoral implant or trial, holding and pulling the femur (a longitudinal force) to distract the femur relative to the acetabulum, and pulling the neck (a lateral force) to distract the femoral implant or trial from the acetabulum; retrieving second coordinates of the femoral head center when the femoral implant or trial is distracted from the acetabulum; and determining a distraction vector based on a difference between the first coordinates and the second coordinates in a coronal plane. In some variations, the intra-operative test may be any kind of shuck test. In still further variations, the method may involve the steps described above performed both before implantation with the native hip and after implantation of the femoral implant or trial.

In some examples, determining the distraction vector may also include: determining a hip offset vector based on a difference between the first coordinates and the second coordinates in the coronal plane along a medial-lateral direction; determining a hip length vector based on a difference between the first coordinates and the second coordinates in the coronal plane along a superior-inferior direction; and combining the hip offset vector and the hip length vector to obtain the distraction vector. In some examples, the method may also include adjustment of the reduced position of the femoral implant or trial or replacement of the femoral implant or trial with one of a different size or geometry when the distraction vector has a magnitude less than 5 mm or greater than 15 mm. In still further examples, adjustment or replacement of the implant or trial may be performed when the distraction vector has a magnitude outside of another range of values.

In some examples, the method may also include adjusting the reduced position of the femoral trial or implant to increase the hip offset and or leg length when the magnitude of the distraction vector is greater than an upper limit of a prescribed safe range, such as 15 mm. In general, a magnitude of an adjustment to increase hip offset and or leg length may be considered as a function of how much the magnitude of the distraction vector is greater than an upper limit of the prescribed range, e.g., 15 mm. For instance, a surgeon may consider more significant increases in hip offset and or leg length when a distraction vector is measured as 22 mm versus a distraction vector measured as 16 mm. Similarly, the method may also include adjusting the reduced position of the trial or femoral implant to decrease the hip offset and or leg length when the magnitude of the distraction vector is less than a lower limit of the prescribed safe range, e.g., 5 mm. For instance, when the lower limit of the prescribed safe range is 5 mm, a surgeon may consider more significant decreases in hip offset and or leg length when a distraction vector is measured as 2 mm versus a distraction vector measured as 4 mm. In further examples, these principles may optionally be employed as specific instructions or recommendations for adjustments based on distraction vector determinations. For instance, a prescribed range of distraction vectors may be set as a safe zone, and instructions for adjustment of hip offset or leg length may be based on how far removed a measured distraction vector is from the prescribed range. In some examples, the determination of specific instructions may be based on empirical data, such as those derived from patients that participate in studies.

In some examples, the method may also include replacing a first head of the femoral implant or trial with a second head larger than the first head when a jump resistance is less than zero, the jump resistance being the magnitude of the distraction vector subtracted from a radius of the first head. In some examples, the method may include, prior to retrieving the first coordinates: placing a fiducial marker on each of the pelvis and the femur; collecting a first plurality of landmarks on the pelvis to register the first plurality of landmarks with a coordinate system; and collecting a second plurality of landmarks on the reduced femoral implant or trial to register the second plurality of landmarks with the coordinate system. In these examples, the first coordinates and the second coordinates are derived from real-time coordinates of the second plurality of landmarks. In still further examples, the trial is intra-operatively reduced into the acetabulum.

In one embodiment, a method of evaluating soft tissue tension in a hip joint of a patient using navigation and software includes steps as follows: retrieving first head center coordinates of a center of a head of a femoral implant or trial when the femoral implant or trial is reduced in an acetabulum of the patient; capturing a real-time location of the head when the head is distracted from its reduced position during performance of a shuck test; determining second head center coordinates of the center of the head while the head is distracted; comparing the second head center coordinates to a peripheral tension-limit boundary of the center of the head based on moving the femur through a range of motion or arc of motion while the femur is distracted; and using a distraction vector defined by a difference between the first head center coordinates and the second head center coordinates to evaluate soft tissue tension when the distraction vector is aligned on an axis passing internal to the peripheral tension-limit boundary.

In some examples, the comparing step may also include comparing the second head center coordinates to a cone-shaped boundary defined by a surface adjoining the peripheral tension-limit boundary with coordinates defining a center of the acetabulum. In some examples the method may also include, prior to using the distraction vector: determining a hip offset vector based on a difference between the first head center coordinates and the second head center coordinates in a coronal plane along a medial-lateral direction; and determining a hip length vector based on the difference between the first head center coordinates and the second head center coordinates in a coronal plane along a superior-inferior direction. The distraction vector is a hypotenuse connecting the hip offset vector and the hip length vector. In a variation of the above examples, the method may also include adjusting the femoral implant or trial to change at least one of a reduction hip offset and a reduction hip length when the axis aligned through the distraction vector passes internal to the peripheral tension-limit boundary and a magnitude of the distraction vector is outside of a specified or prescribed range, e.g., from 5 mm to 15 mm.

In further examples, the method may also include repeating the shuck test when the axis aligned through the distraction vector passes on or external to the peripheral tension-limit boundary. In some examples, performance of the shuck test may involve: gripping a neck of the femoral implant or trial; holding and pulling the femur to distract the femur relative to the acetabulum; and laterally pulling the neck of the femoral implant to distract the femoral implant or trial from the acetabulum. In other examples, performance of the shuck test may involve: gripping a neck of the femoral implant or trial; manipulating a leg extending from the hip joint so that the leg is abducted and rotating the leg about its axis at least 10 degrees; and while holding the leg in a manipulated position based on the manipulating step, pulling the neck to distract the femoral implant or trial from the acetabulum.

In further examples, the method may also include: repeating the shuck test when the direction of the distraction vector is oriented at an angle on or outside a range-of-motion cone defined by a surface extending between the peripheral tension-limit boundary and a center point of the acetabulum. In some examples, the method may also include: adjusting at least one of the reduced hip offset and the reduced hip length to a revised reduced hip offset and a revised reduced hip length when the magnitude of the distraction vector is less than 5 mm or greater than 15 mm so that a combined revised reduced hip offset and revised reduced hip length is closer to the pre-operative hip offset and pre-operative hip length than the reduced hip offset and reduced hip length.

In one embodiment, a method of evaluating soft tissue tension surrounding a hip of a patient during an implant replacement procedure is performed with the use of navigation and software to track positions of a femur and an acetabulum of a patient in real time. The method includes: dislocating the femur relative to the acetabulum; retrieving first coordinates of a center of the acetabulum; performing an intra-operative test to bring soft tissue of the patient into tension, the testing involving holding and pulling the femur to distract the femur relative to the acetabulum; retrieving second coordinates of a femoral head center of a femoral implant based on a position of the femoral implant when the femoral implant is disposed in the femur while the femur is distracted relative to the acetabulum; and determining a distraction vector based on a difference between the first coordinates and the second coordinates in a coronal plane.

In some examples, the method may also include, prior to retrieving the first coordinates: placing a fiducial marker on each of the femur and a pelvis of the patient; collecting a first plurality of landmarks on the pelvis to register the first plurality of landmarks with a coordinate system; and collecting a second plurality of landmarks on the reduced femoral implant to register the second plurality of landmarks with the coordinate system. In these examples, the first coordinates and the second coordinates are derived from real-time coordinates of the second plurality of landmarks.

In some examples, performing the intra-operative test may also include pulling the femur while monitoring a force associated with the pulling. In some examples, performing the intra-operative test may also include pulling the femur using a controlled force. In some examples, performing the intra-operative test may also include monitoring a magnitude and direction of a distraction from an acetabular cup center of the acetabulum on a display. In some examples, the method may also include, prior to performing the test, cutting a ligamentum teres of the patient to separate the femur and the acetabulum. In some examples, the method may also include, prior to performing the test, resecting a neck of the femur. In some examples, the method may also include reducing the femoral implant in the acetabulum such that the first coordinates are retrieved when the femoral implant is reduced in the acetabulum. In some examples, the method may also include reducing the first femoral implant in the acetabulum such that the first coordinates are retrieved when the femoral implant is reduced in the acetabulum. In some examples, the method may also include displaying on a user interface the first coordinates, the coordinates of the femoral head center and a real time distraction vector during the performance of the intra-operative test. In some examples, the method may also include selecting and virtually reducing the femoral implant into the acetabulum prior to retrieving the first coordinates. In some examples, retrieving the second coordinates of the femoral head center may also include retrieving third coordinates of a known location on the femur in the distracted position and determining the second coordinates based on a virtual location of the femoral head center relative to the third coordinates.

In one embodiment, a method of evaluating soft tissue tension in a hip joint of a patient using navigation and software includes the following steps: retrieving first coordinates of a center of an acetabulum of the patient; dislocating a femur of the patient relative to the acetabulum; performing an intra-operative test to bring soft tissue of the patient into tension, the test including: gripping at least part of the femur, pulling the femur to distract the femur from the acetabulum, and while the femur is distracted, pulling the femur into a plurality of orientations such that each orientation of the plurality of orientations of the femur is at a different angle relative to a central acetabular axis through a center of the acetabulum, wherein femoral head center coordinates of a femoral implant based on the femoral implant being positioned in the femur are retrieved at each orientation of the plurality of orientations of the femur to define a envelope; determining an intersection of the central acetabular axis and the envelope to define second coordinates; and determining a distraction vector based on a difference between the first coordinates and the second coordinates in a coronal plane. In some variations, the pulling of the femur into a plurality of orientations amounts to the performance of a plurality of shuck tests, and the combined femoral head center coordinates define a shuck envelope.

In some examples, pulling the femur in a plurality of directions may also include pulling in anterior, posterior, medial and lateral directions to reach soft tissue restraints of the hip joint. In some examples, the method may also include, prior to performing the intra-operative test, resecting a neck of the femur. In some examples, the method may also include implanting the femoral implant in the femur prior to performing the intra-operative test. In some examples, femoral head center coordinates may be retrieved at each orientation of the plurality of orientations based on retrieving third coordinates of a known location on the femur for each of the plurality of orientations and determining respective femoral head center coordinates based on a virtual location of the femoral head center relative to the third coordinates when a virtual femoral implant is positioned in the femur.

In one embodiment, a method of evaluating soft tissue tension in a hip joint of a patient using navigation and software includes performing the method when the patient anatomy is registered with a single registration marker on the pelvis. In one example, the femur may be set up for monitoring by using a femoral checkpoint. With the pelvis registered, a probe connected to the navigation system collects the femoral checkpoint on the femur so that a real-time location of the femoral checkpoint may be monitored through its location relative to the pelvis. In the method, an intra-operative test may be performed to bring soft tissue of the patient into tension, the test including: gripping at least part of the femur, pulling the femur to distract the femur from the acetabulum, and capturing coordinates of the femoral checkpoint while the femur is distracted. The femoral checkpoint may be initially located so that locations of other areas of the femoral anatomy are known relative to the checkpoint, and in the same way, dimensions and relative locations of a trial or femoral implant, including head center, may also be derived from the checkpoint real-time location. This may be done with a physical trial or implant in the femur, or through a virtual representation of an implant in the femur. In this manner, the shuck test may be performed with this workflow, i.e., without registration of the femur, and a distraction vector may be obtained with the navigation system based on a comparison of initial and distraction coordinates. It should also be appreciated that the method may be modified as necessary to account for any errors in the measurements that may result from rotation of the femur during the test. For example, by finding the minimum distance through a femoral rotation at the distraction position of the femur.

In one embodiment, the present disclosure relates to a method of evaluating soft tissue tension surrounding a hip of a patient during an implant replacement procedure, where the method involves the use of navigation and software. Steps of the method may include: tracking positions of a femur and an acetabulum of the patient in real-time based on registration of the femur and a pelvis of the patient; dislocating the femur relative to the acetabulum; retrieving first coordinates of a center of the acetabulum; performing an intra-operative test to bring soft tissue of the patient into tension comprising holding and pulling the femur to distract the femur relative to the acetabulum; retrieving a virtual femoral implant and overlaying the virtual femoral implant in an implanted position on a virtual representation of the femur based on the registration of the femur; retrieving second coordinates of a first tracked location on the femur while the femur is distracted relative to the acetabulum and determining third coordinates of a virtual location of a femoral head center of the virtual femoral implant based on a relationship between the third coordinates and the second coordinates; and determining a distraction vector based on a difference between the first coordinates and the third coordinates in a coronal plane.

In another aspect, the present disclosure relates to a method of evaluating a completed intra-operative test. In one embodiment, the method may include: displaying a virtual cone defined by a surface between a tip and a base, the tip being a center of an acetabulum of a patient and the base being a perimeter of a plurality of femoral implant head center locations determined based on moving a femur of the patient through a range of motion about a pelvis of the femur while soft tissue connecting the femur to the pelvis is in tension; displaying a vector including a magnitude with a first end at the center of the acetabulum and a second end opposite the first end, the vector and the virtual cone being in a first coordinate space; and determining whether an axis through the first end and the second end passes through the surface. The vector may be determined based on the femur being tensioned relative to the acetabulum. In some examples, the method may also include comparing the magnitude to a prescribed range of magnitudes to determine whether the magnitude is within the prescribed range of magnitudes, the prescribed range representing balanced soft tissue in a hip joint.

In yet another aspect, the present disclosure relates to a system configured to evaluate soft tissue tension in a hip of a patent. In a first embodiment, a system includes a computer with a processor and a memory, a sensor in operative communication with the computer, first and second trackers, and a pointer tool. The first tracker may be configured to be affixed to a pelvis of the patient, the first tracker being in operative communication with the sensor. The second tracker may be configured to be affixed to a femur of the patient, the second tracker being in operative communication with the sensor. The pointer tool may be configured to register at least one landmark on a surface of the femur such that a location of a femoral head center of a femoral implant or trial relative to one of the first tracker and the second tracker is known in real-time, the femoral implant or trial being implanted in the femur. The computer may be configured to receive first coordinates of the femoral head center when the femur is reduced in an acetabulum of the pelvis and to receive second coordinates of the femoral head center when the femur is pulled away from the acetabulum such that soft tissue connecting the pelvis to the femur is in tension. And, the computer may be configured to determine a distraction vector based on a difference between the first coordinates and the second coordinates.

In a second example, the system of the first example includes a computer that may be configured to recognize a predetermined range of distraction vector magnitudes and to output whether a determined distraction vector is within the predetermined range. In a third example, the predetermined range of distraction vector magnitudes of the second example is in a range from 5 mm to 15 mm. In a fourth example, the system of any one of the first through third examples includes a computer that may be configured to: determine a hip offset vector based on a difference between the first coordinates and the second coordinates in a coronal plane along a medial-lateral direction; determine a hip length vector based on a difference between the first coordinates and the second coordinates in the coronal plane along a superior-inferior direction; and combine the hip offset vector and the hip length vector to obtain the distraction vector. In a fifth example, the system of any one of the first through fourth examples may include a computer configured to collect a plurality of additional coordinates of the femoral head center when the femur is pulled away from the acetabulum in different directions while the soft tissue connecting the pelvis to the femur is in tension, the plurality of additional coordinates defining a perimeter such that a conical volume is defined by the perimeter and the first coordinates. In a sixth example, the system of any one of the first through fifth examples may include a pointer configured to register at least two landmarks on the femur such that processing of such landmarks by the processor provides the location of the femoral head center.

In another aspect, the present disclosure relates to a non-transitory computer-readable medium whose contents enable a navigation system to determine a distraction vector representing a change in a position of a femur relative to a pelvis by performing a method. In a first example, a non-transitory computer-readable medium whose contents enable a navigation system to determine a distraction vector representing a change in a position of a femur relative to a pelvis by performing a method involves a method including: retrieving first coordinates of a femoral head center of a femoral implant or trial using a sensor and a trackable marker of a navigation system in response to the femoral implant or trial being intra-operatively reduced into a reduced position in an acetabulum of a patient; retrieving second coordinates of the femoral head center using the sensor and the trackable marker in response to the femoral implant or trial being distracted from the acetabulum such that soft tissue connecting the femur to the pelvis is brought into tension; and determining, using a computer of the navigation system, the distraction vector based on a difference between the first coordinates and the second coordinates in a coronal plane.

In a second example, the non-transitory computer-readable medium of the first example has contents that enable the navigation system to perform a method that may include receiving a signal that the femoral implant or trial is distracted and retrieving the second coordinates in response. In a third example, the non-transitory computer-readable medium of the first or second example has contents that enable the navigation system to perform a method that may include determining the distraction vector by: determining a hip offset vector based on a difference between the first coordinates and the second coordinates in the coronal plane along a medial-lateral direction; determining a hip length vector based on a difference between the first coordinates and the second coordinates in the coronal plane along a superior-inferior direction; and combining the hip offset vector and the hip length vector to obtain the distraction vector. In a fourth example, the non-transitory computer-readable medium of any one of the first through third examples has contents that enable the navigation system to perform a method that may include retrieving a plurality of distraction coordinates in response to movement of the femur through a range of motion while distracted from the pelvis with the soft tissue in tension, the plurality of distraction coordinates collectively defining a peripheral tension-limit boundary of the femoral head center.

BRIEF DESCRIPTION OF THE DRAWINGS

A more complete appreciation of the subject matter of the present disclosure and of the various advantages thereof can be realized by reference to the following detailed description in which reference is made to the accompanying drawings in which:

FIG. 4 is a table of demographic and other information of patients that were the subject of a shuck test study.

FIG. 5 is a table including intra-operative and pre-operative hip information of patients according to the study referenced in FIG. 4.

FIG. 6 is a table including information derived from shuck tests performed on patients according to the study referenced in FIG. 4.

DETAILED DESCRIPTION

In one aspect, the present disclosure relates to a method of evaluating tissue tension in a hip joint. While certain embodiments in the present application are described as methods involving surgery in the hip, the contemplated procedures may also be employed in other ball-and-socket joints such as the shoulder. In one embodiment, a method commences with a patient pelvis and femur registered with a navigation system such that locations on the pelvis and femur are monitored real-time. In this way, a surgeon will have joint component location information available for viewing or retrieval in an intra-operative setting. Additionally, in this method, a pre-operative hip offset and hip length on both sides of the joint is already determined.

Optionally, the method may be preceded by a step of registering the patient anatomy with the navigation system. The process of registration may initially involve pre-operative planning with the capture of a CT scan of the patient and the creation of a virtual 3D model of the pelvis and femur. Landmarks on the pelvis and femur may be identified at this time for later registration. These may include landmarks on both acetabular surfaces and at various locations on each femur, including the femoral head, the lesser trochanter, and locations that allow for the calculation of the longitudinal axis of the femur. With the anatomical data analyzed in this pre-operative planning stage, the pre-operative hip offset and hip length may be determined using the model. During an intra-operative stage of the procedure, fiducial markers are placed on the pelvis and the femur, respectively. Landmark points on the femur may then be collected to register the femur. These landmarks may include points on the femoral head, neck and areas distal to the neck. Similarly, landmark points on the pelvis, and in particular in and around the acetabular surfaces may also be collected to register the pelvis. The collection process may be accomplished by tapping a probe connected to the navigation system on the landmarks. With the completion of these steps, the pelvis and the femur of the patient may be monitored real-time.

Figure 13:
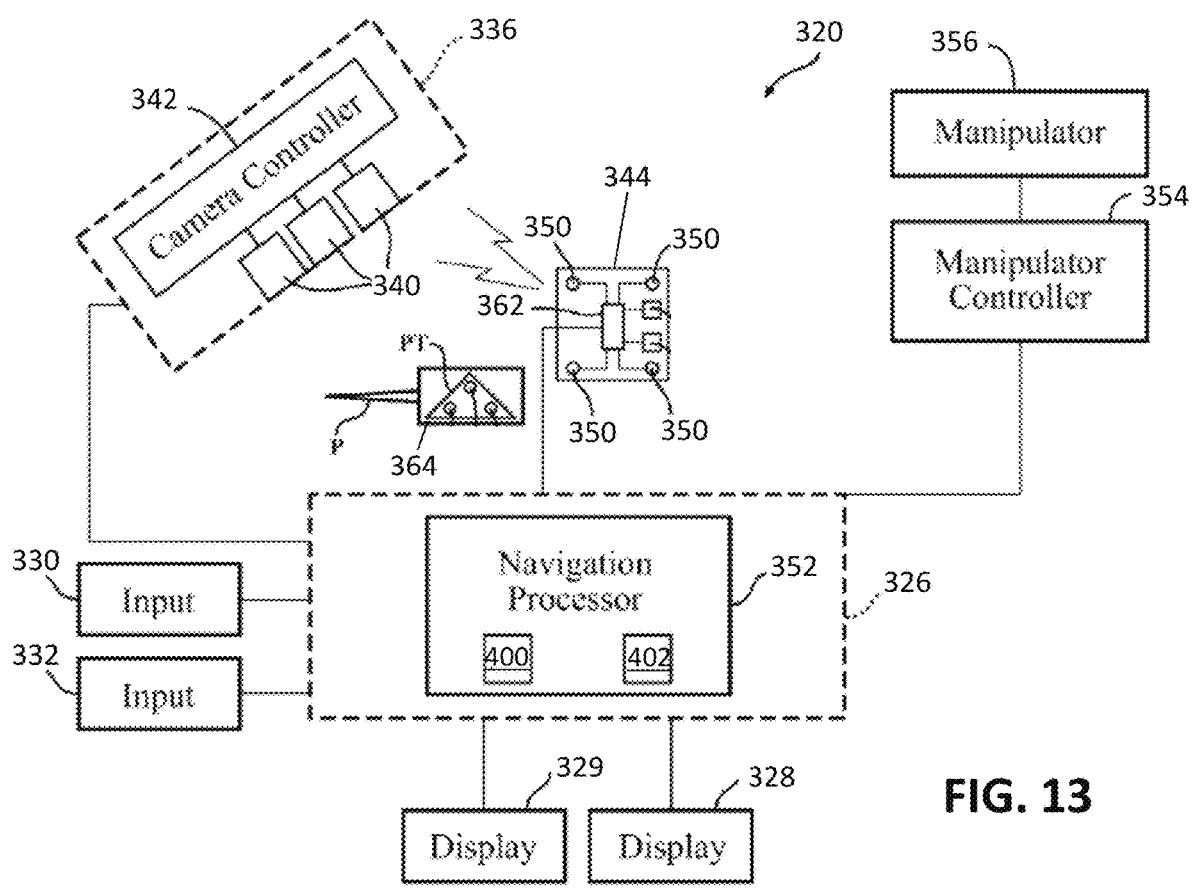
FIG. 13 is a schematic view of a navigation system according to one embodiment of the disclosure.

Returning to the patient having a registered pelvis and femur, a hip replacement may proceed with a femoral neck resection and broaching or other technique to prepare the femoral canal to receive a trial and/or femoral implant. For the sake of brevity, the remainder of the description of this embodiment will refer to an implant, though it should be appreciated that a trial may also be used. With an implant disposed at a desired position relative to the femur, the location of such implant may also be monitored real time. This may be through a fiducial marker on the implant itself, or through registration of a landmark or landmarks on the implant. In each approach, all fiducial markers should be visible to the camera of the system. One exemplary system that may be used to perform the above-described registration is the Mako™ THA 4.0 System, by Stryker®. Additionally, another exemplary system is shown in FIG. 13 and described below.

Figure 1:
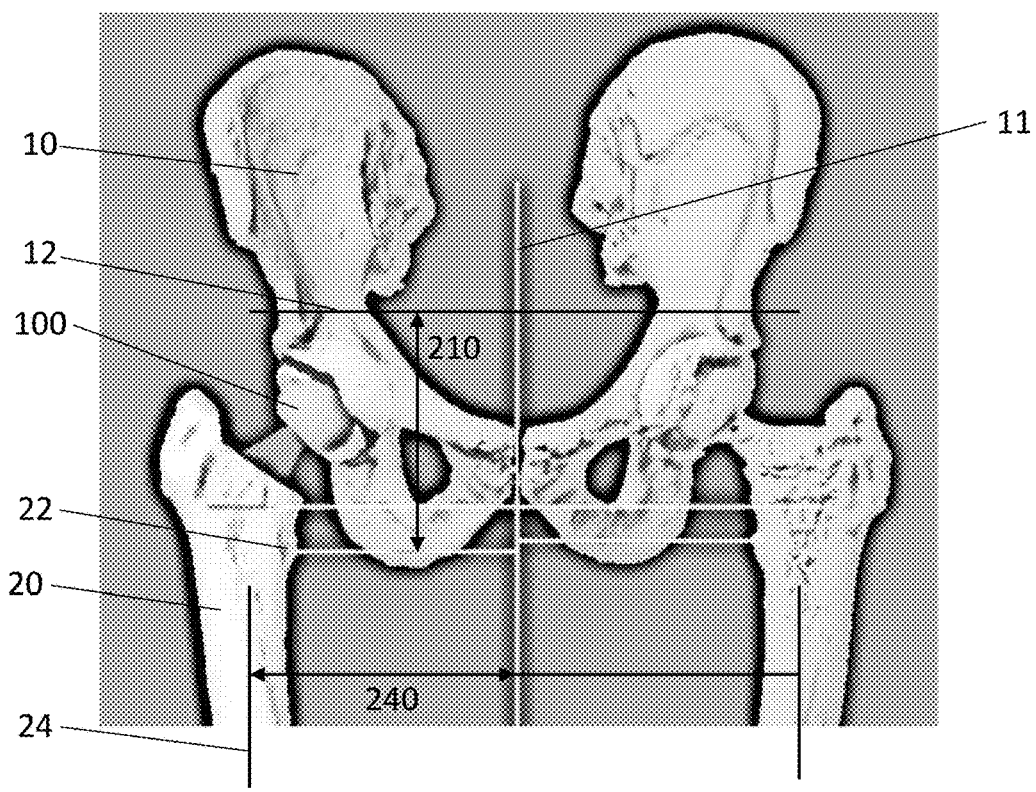
FIG. 1 is a front view of a hip joint with a reduced femur according to one embodiment of the disclosure.

When the implant is disposed in a desired manner in the femur and registered, the femur 20 is reduced into the acetabulum of the pelvis 10 as shown in FIG. 1. In this position, a reduced hip offset 240 and reduced hip length 210 are determined, where hip offset 240 is measured from a midline axis 11 to a femoral canal axis 24 and hip length 210 is measured from ASIS axis 12 to a lesser trochanter 22 of the femur in a superior-inferior direction. With intra-operative reduced hip offset and hip length and pre-operative hip offset and hip length both determined, an evaluation may be made as to whether the results are satisfactory based on any changes resulting from the reduction or any inequality on opposite sides of the hip. During this time, a shuck test may be performed while monitoring real-time locations on the pelvis 10, femur 20 and implant 100 with the navigation system to evaluate soft tissue balancing in the hip. This may be performed on one or both sides of the hip, depending on the specifics of the circumstances, but the procedure will be the same in either case.

The shuck test is performed in a manner as understood by persons of skill in the art. In one example, the femur is gripped and then pulled to distract the femur from the acetabulum and to place soft tissue around the hip joint in tension. In another example, the leg extending from the hip joint under consideration is positioned by a first person in approximately 40 degrees of flexion to relax the anterior capsule of the patient and in neutral rotation and abduction. A second person positions a bone hook around a femoral neck of the implant to provide offset traction and the first person provides axial traction. In some examples, the two persons may include the surgeon and an assistant. Other known approaches to drawing the femoral head out from the acetabular socket may also be employed.

Figure 2:
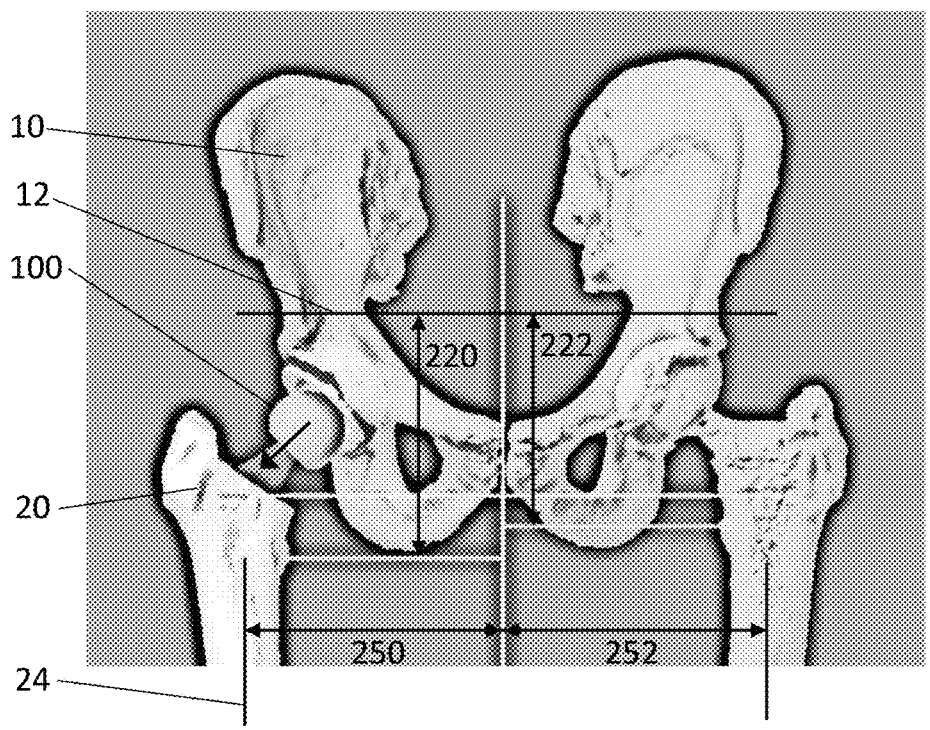
FIG. 2 is a front view of the hip joint of FIG. 1 during performance of a shuck test.

One example of the distraction that occurs during performance of the shuck test is shown in FIG. 2. While a femoral head of the femur is distracted, new measurements are retrieved including hip offset 250 and hip length 220. FIG. 2 illustrates how hip offset 250 and hip length 220 are greater than hip offset 240 and hip length 210 determined when the joint is reduced as shown in FIG. 1.

Figure 3:
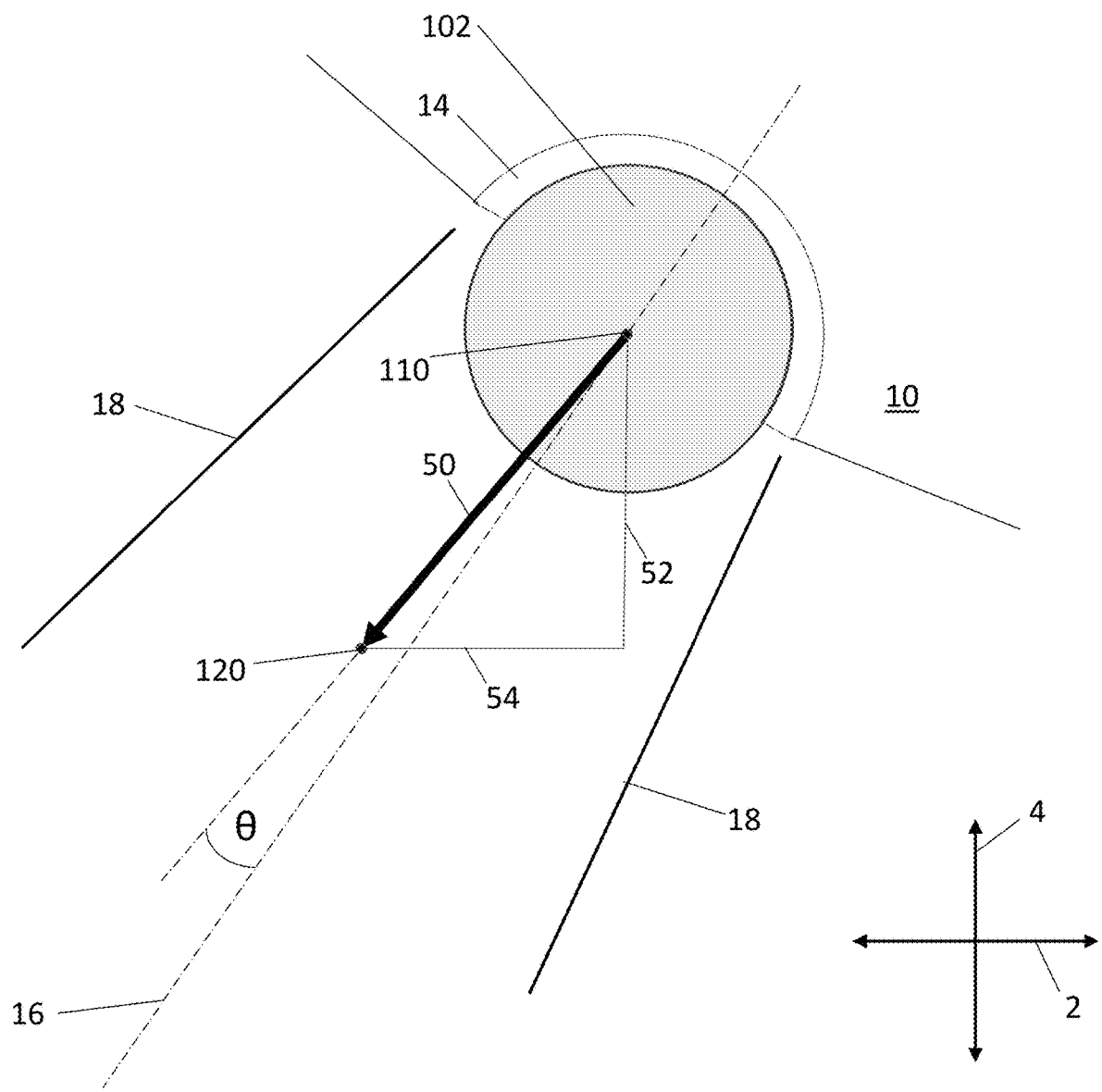
FIG. 3 illustrates measurements in a hip joint captured through the performance of a shuck test according to embodiments of the disclosure.

Because locations on the pelvis, femur, and femoral implant are registered in a global coordinate system that is monitored via the navigation system, an objective comparison may be made between the reduced and distracted position of the femoral implant. Certain measurements obtained through such comparison are shown in FIG. 3. Specifically, while the implant is in the reduced position, coordinates of a femoral head 102 surface of implant 100, along with a reduced femoral head center 110, are determined and stored. With the aforementioned data points as a foundation, when the shuck test is performed, femoral head 102 is distracted from acetabulum 14 until reaching shuck test center 120. During the test, the navigation system may monitor real-time distraction magnitude. Additionally, the software of the navigation system may be configured to monitor the force applied through pulling of the femur axially, axially and laterally, or any combination of directions. In some examples, the software may be configured to output audio or visual signals through a user-interface available to the surgeon where the signals are set to activate when forces approach outer bounds of a desired range of pull force. Such signals may assist the surgeon in maintaining the force within the desired range. Upon completion of the shuck test, the coordinates of shuck test center 120 are then compared to reduced center 110.

In some variations of the method, a peripheral tension-limit boundary, also referred to as a directional soft-tissue restraint limit boundary, of the femoral head center is also determined during performance of the shuck test or shortly before or after. The peripheral tension-limit boundary represents a range of shuck length values based on pulling the femur in different directions relative to a center axis of the acetabulum. The shuck length values may be retrieved by moving the femur through a range of motion or arc of motion while the femur is pulled relative to the pelvis, for example. The peripheral tension-limit boundary may include shuck length vectors with end points that, when combined, define a virtual surface enclosed by a perimeter that is located in space at a distance from a center of the acetabular cup that is generally similar to a distance of an aggregation of various shuck length vectors retrieved based on shuck tests performed at different femur angles. Put another way, the peripheral tension-limit boundary may be spaced from the acetabulum at a distance approximately corresponding to the various shuck length vector magnitudes. In some examples of these variations, the peripheral tension-limit boundary may collectively define a shuck envelope that is the virtual surface representative of all of the distraction values. In other examples, the peripheral tension-limit boundary may form a base of a shuck cone having a tip defined by a center of an acetabulum of the patient. In this manner, the cone is "filled-in" between the base and tip by an outer surface connecting the two with a volume therein. The shuck cone, including virtual representations of the cone, may be representative of the soft tissue-imposed limits on movement of the femur. This is shown by cone 18 in FIG. 3, for example, where a base of cone 18, not shown but located toward a wide end of cone 18, represents the outer bound of distraction of the femur when performing shuck tests in different directions. The above determinations of an envelope and or cone volume may be made with shuck tests performed with physical implants or trials, or with a virtual implant. Data collected to define the peripheral tension-limit boundary may be processed with the navigation system and associated software to generate the envelope or cone.

To compare shuck test center 120 with reduced femoral head center 110, a delta hip length 52 is determined based on a difference in coordinates in a superior-inferior direction 4 of the patient. Similarly, a delta hip offset 54 is determined based on a difference in coordinates in a medial-lateral direction 2. Through basic trigonometry as applied to a right-angle triangle, these values are combined, as shown in FIG. 3, to obtain a shuck length vector 50, a hypotenuse in a triangle encompassing the three values. Shuck length vector 50 has a magnitude commensurate with the relevant distraction from the performance of the shuck test. The shuck length vector is a form of distraction vector. Additionally, through the requisite calculations used to arrive at the determination of the shuck length vector, its direction is known as well. This direction may be compared with center axis 16 of the acetabulum 14, or a center axis of an implanted acetabular cup in some examples, to determine how successfully the shuck length test was performed. In the illustration of FIG. 3, angle $\theta$ represents a difference in angulation between shuck length vector 50 and center axis 16. In some examples, cone 18 may be used as a further guide to evaluate the sufficiency of the direction of the shuck length vector based on the shuck test.

Results of the shuck test may be used to evaluate soft tissue tension in the joint and may further be used to make adjustments to improve outcomes, the guidance for such adjustments being supported by a study encompassed within the present disclosure. Illustrations of how the results of the shuck test may be used according to the present embodiment include the following. First, angle $\theta$ may be considered to determine whether the shuck test was performed in a sufficiently accurate manner to rely on the result. For instance, if angle $\theta$ is 60 degrees and such angle projects an axis through the shuck length vector outside of cone 18, the shuck test should be performed again to obtain a more reliable result. Second, under circumstances where the direction of the shuck length vector is not a concern, the magnitude of the shuck length vector may be used to assess the sufficiency of soft tissue tension in the joint. As described in greater detail elsewhere in the disclosure in the results of the study, an acceptable safe zone of shuck length vector magnitude may be a prescribed range based on test data or other factors. In one example, a safe zone may be between 5 mm and 15 mm. Thus, if a shuck length vector magnitude falls within this range, it indicates to the surgeon that soft tissue tension will not impede the completion of surgery based on an already established implant reduction position. However, if the magnitude of the shuck length vector is outside of the prescribed range, e.g., less than 5 mm or greater than 15 mm, such values indicate that tissue tension may be too high or too low.

The results of the study, again, discussed in greater detail elsewhere in the disclosure, support a conclusion that there is an inverse relationship between magnitude of a shuck length vector and combined reduced hip length and offset relative to the preoperative condition. Thus, if a shuck length vector magnitude is 20 mm for example, a surgeon may consider reducing such magnitude by adjusting the joint to increase the combined reduced hip length and offset. And, the opposite approach would apply if the magnitude is less than 5 mm. In such case, the surgeon would consider increasing the magnitude of the shuck length vector by decreasing the combined reduced hip length and offset. Or, alternatively, adjustments to offset by itself have been found to have a similar inverse correlation. A surgeon may use a variety of approaches to make adjustments. For example, if a femoral implant or trial is used for performance of the shuck test, a femoral head of a different size may be substituted for the existing femoral head. For trials with a modular neck and modular stem, a neck, stem or neck and stem with different sizes may be substituted for existing components in a similar manner. It should be appreciated that these examples are merely illustrative and that other techniques used by surgeons to adjust hip length, offset and other hip joint measures may also be used.

The study contemplates specific relationships based on analysis of patient data, and the equations below capture these findings as one example of how objectively measured shuck length has been found to relate to reduced hip joint measurements:

$$\text{Shuck Length} = -0.4[\Delta(\text{Reduced } HL+OS \text{ vs. pre-op } HL+OS)]+10.5$$

$$\text{Shuck Length} = -0.6[\Delta(\text{Reduced } OS \text{ vs. pre-op } OS)]+9.0$$

In this manner, the equations may serve as one example guide on how adjustments to the hip implant may improve soft tissue balance in the joint.

Moreover, the results of the shuck test may also be used to evaluate what is known as jump resistance, which is equal to the magnitude of the shuck length vector subtracted from the head radius of the femoral implant. This value may be insightful to evaluate potential issues with bone impingement or the fit of the implant in the joint more generally including potential risk of dislocation in the joint. Jump resistance values greater than zero suggest a decreased risk of dislocation in the joint. In these instances, a dome of the femoral head remains below an acetabular liner rim during the shuck test. Jump resistance values less than zero should prompt consideration of further adjustment to the reduced position of the femoral implant.

In one embodiment, a method of evaluating tissue tension in a hip joint may be performed without the use of physical implants. In this method, the pelvis and the femur are registered as described elsewhere in the disclosure so that physical locations on the pelvis and femur may be monitored real-time. Along with such monitoring, models of the pelvis and femur may be generated for output on a user-interface to view the anatomy. And, in conjunction with the virtual bone models, virtual models of a femoral implant or a femoral implant and an acetabular implant may be generated in the model to evaluate placement virtually. This may all be done within an intra-operative setting. With this foundation, the femur may be dislocated relative to the acetabulum and the femoral head may be resected to perform the shuck test. Although the shuck test itself would not provide a shuck length vector, one or more implant models may be incorporated into the bone model during the performance of the shuck test to visualize what a magnitude of the shuck length vector would be with that implant, fit virtually within a femur. In conducting such analysis, a surgeon may intra-operative substitute one virtual implant for another if doing so would provide a more optimal magnitude for the shuck length vector.

In some embodiments, the method of evaluating tissue tension may be accompanied by one or both of software and hardware to present real-time output for a surgeon or another user in an intra-operative setting. Such software may, for example, include an output onto a user interface that indicates shuck values, a shuck length vector and a cone representing a shuck volume indicative of an outer bound of shuck values, an axis through a center of the acetabulum, or another desired center, as a surgeon performs and completes the shuck test. In this manner, a surgeon may obtain additional information during a procedure as to whether the shuck test is proceeding as desired and provides additional information helpful to determine whether it would be most productive to commence the test again. In one variation, the display includes an interactive button that may, for example, allow the surgeon to select the coordinates at a maximum extent of the shuck test to save them digitally for later use. This software and hardware may be standalone or it may be incorporated or in communication with the navigation system.

In a specific example, values of the acetabular cup center, the femoral head center, or other values monitored through the navigation system, may be displayed to a surgeon real-time in an operative setting. Display may be numerical, through a visual model, or both. Values obtained during the procedure, including those retrieved during the shuck test, may be saved in any manner desirable for later use.

In another aspect, the present disclosure relates to a system that includes hardware adapted to run software to perform methods as contemplated by the present disclosure. For example, systems adapted to track movement of anatomy during surgery. In some embodiments, such systems may be in the form of navigation system 320 shown in FIG. 13. Anatomy may include, for example, the femur and the pelvis. In some examples, navigation system 320 may include a navigation computer 326, a sensor and a tracker. In some examples, navigation system 320 may include a navigation computer 326, one or more displays 328, 329, one or more inputs 330, 332, such as a mouse and keyboard, a sensor, such as optical sensing device 336, one or more trackers 344 and one or more pointers 364, all of which are operatively connected to the navigation computer. Optionally, the system may also include a robotic manipulator 356 with a controller 354. Such manipulator may be a cutting tool for use during a procedure, for example.

An optical sensing device 336 communicates with the navigation computer 26. The optical sensing device may include a camera or cameras. The optical sensing device 336 has an outer casing that houses one or more optical position sensors 340. In some embodiments at least two optical sensors 340 are employed, preferably three. The optical sensors 340 may be three separate charge-coupled devices (CCD). In one embodiment three, one-dimensional CCDs are employed. It should be appreciated that in other embodiments, separate camera units, each with a separate CCD, or two or more CCDs, could also be arranged around the operating room. The CCDs detect infrared (IR) signals.

Optical sensing device 336 may be mounted on an adjustable arm to position the optical sensors 340 with a field of view of the below discussed trackers that, ideally, is free from obstructions.

The optical sensing device 336 includes a camera controller 342 in communication with the optical sensors 340 to receive signals from the optical sensors 340. The camera controller 342 communicates with the navigation computer 326 through either a wired or wireless connection (not shown). One such connection may be an IEEE 1394 interface, which is a serial bus interface standard for high-speed communications and isochronous real-time data transfer. The connection could also use a company specific protocol. In other embodiments, the optical sensors 340 communicate directly with the navigation computer 326.

Position and orientation signals and/or data are transmitted to the navigation computer 326 for purposes of tracking the objects. A computer cart assembly to support the computer and display of the system, display 328, 329, and optical sensing device 336, where included, may be like those described in U.S. Pat. No. 7,725,162 (the '162 patent), hereby incorporated by reference herein in its entirety.

The navigation computer 326 may be a personal computer or laptop computer. Navigation computer 326 may have the displays 328, 329, central processing unit (CPU) and/or other processors, memory (not shown), and storage (not shown). The navigation computer 326 is loaded with software as described below. The software converts the signals received from the optical sensing device 336 into data representative of the position and orientation of the objects being tracked.

Tracking device 344 is also referred to herein as a tracker. In a procedure involving dislocation of the hip, one tracker 344 is firmly affixed to the femur of the patient and another tracker is firmly affixed to the pelvis of the patient. Trackers are firmly affixed to sections of bone. Trackers may be attached to bone as described in U.S. Pat. App. Pub. No. 2014/0200621 (the '621 Publication), hereby incorporated by reference herein in its entirety, or through other tracker affixation techniques as well known in the art.

The optical sensors 340 of the optical sensing device 336 receive light signals from the tracker or trackers. In FIG. 13, tracker 344 is an active tracker. In some examples, active trackers may include active markers in the form of light emitting diodes. In other embodiments, the tracker 344 may have passive markers (not shown), such as reflectors that reflect light emitted from the optical sensing device 336. The reflected light is then received by the optical sensors 340. Active and passive marker arrangements are well known in the art.

In some examples, tracker 344, or any other tracker, may include one or more of a tracker controller, a gyroscope sensor and an accelerometer, as well known in the art.

The navigation computer 326 includes a navigation processor 352. The optical sensing device 336 receives optical signals from the LEDs 350 of the trackers 344 and outputs to the processor 352 signals and/or data relating to the position of the LEDs 350 of the trackers 344 relative to the optical sensing device 336. Relative orientations may also be determined through the use of gyroscope sensors.

Navigation system 320 monitors the positions of the pelvis and femur of the patient by monitoring the position of bone trackers firmly attached to bone. For example, through respective trackers attached to the pelvis and the femur.

Prior to the start of the procedure, pre-operative images of the femur and pelvis are generated (or of other tissues in other embodiments). These images may be based on magnetic resonance imaging (MRI) scans, radiological scans or computed tomography (CT) scans of the patient's anatomy. These images are mapped to the femur coordinate system and pelvic coordinate system using well known methods in the art. In one embodiment, a pointer instrument P, such as disclosed in the '162 patent, having its own tracker PT (see pointer 364 in FIG. 13), may be used to map the femur coordinate system and pelvic coordinate system to the pre-operative images. These images are fixed in the femur coordinate system and pelvic coordinate system. Conversion of data points in these coordinate systems may be performed with a coordinate transformer.

As to processing of received location data via software, navigation computer 326 includes a localization engine 400 and a coordinate transformer 402. With continued reference to FIG. 13, a localization engine 400 is a software module that may be considered part of the navigation system 320. Components of the localization engine 400 run on navigation processor 352. In some versions, the localization engine 400 may run on the manipulator controller 354.

Localization engine 400 receives as inputs the optically-based signals from the camera controller 342 and the non-optically based signals from the tracker controller 362. Based on these signals, localization engine 400 determines the position and orientation of bone tracker coordinate systems for the pelvis and femur in a localizer coordinate system. The localizer coordinate system has an origin and an orientation (a set of x, y and z axes). When an instrument is used in system 320, localization engine 400 operates in a similar manner utilizing signals received from a tracker on the instrument.

The localization engine 400 forwards the signals representative of the positions and orientations of the trackers on the pelvis and femur to a coordinate transformer 402. Coordinate transformer 402 is a navigation system software module that runs on navigation processor 352. Coordinate transformer 402 references the data that defines the relationship between the pre-operative images of the patient and the patient trackers. Where applicable, coordinate transformer 402 also stores the data indicating the position and orientation of the working end of a surgical instrument relative to the instrument tracker.

During the surgical procedure, coordinate transformer 402 receives the data indicating the relative positions and orientations of the trackers to optical sensing device 336. Based on these data and the previously loaded data, the coordinate transformer 402 generates data indicating the relative position and orientation of both the pelvic and femoral coordinate systems to the localizer coordinate system. This process ensures that the relevant anatomy, including the pelvis and femur, may be effectively monitored. Accordingly, through the described navigation system 320, a real-time location of target locations on the femur or pelvis may be captured and recorded, thereby providing data to perform the methods described herein.

Further details regarding this example navigation system may be found in the '621 Publication, hereby incorporated by reference herein in its entirety.

Experimental Results: Study

A study was performed that included 61 patients who were a subset of a larger population of patients. Primary robotic assisted total hip arthroplasty ("THA") was performed by a single surgeon via a posterior approach and no anterior capsule or psoas release was performed. Fiducial markers and registration procedures were employed to obtain anatomical measurements and collect data more generally with the use of the enhanced protocol of the Mako™ THA 4.0 System by Stryker®, with features as already described elsewhere in the present disclosure. The implants used for the study included the Stryker® Accolade™ II uncemented femoral stem and the Stryker® Trident™ System for the acetabular components. Head sizes for the femoral implants were chosen at the surgeons discretion, and included those having 32 mm and 36 mm diameters.

For each patient assessed as part of the study, the shuck test was performed as known to persons of skill in the art and was performed after implantation of the definitive components but before posterior capsular repair. The leg was positioned in approximately 40 degrees of flexion to relax the anterior capsule and in neutral rotation and abduction. The operative surgeon placed a bone hook around the femoral neck to provide offset traction and an assistant provided axial traction.

Data collected for each patent as part of the study included patient demographics; femoral implant details; pre-operative hip offset and pre-operative hip length; intra-operative hip offset and intra-operative hip length and shuck values for the hip length and offset, with trigonometry used to calculate a shuck length vector, the shuck length vector being compared to measurements of the ipsilateral and contralateral hip. Demographic details of the patients included in the study are shown in FIG. 4. Where applicable, the severity of ipsilateral and contralateral hip arthritis was assessed as per the Tonnis classification.

To advance the aims of the study, the collected data was processed so that shuck length values could be compared and related to hip measurements of respective patients. This in turn allowed for a determination of whether and to what extent there are relationships between shuck length values and the anatomy of a patient hip. Throughout the disclosure, the abbreviation "HL" is used interchangeably with "hip length" and the abbreviation "OS" is used interchangeably with "hip offset."

Data for all patients of the study was aggregated to determine average values and a magnitude of one standard deviation of the values. The data includes pre-operative hip length compared to a contralateral hip, pre-operative hip offset compared to a contralateral hip, intra-operative reduced hip length compared to pre-operative hip length ($\Delta$(Reduced HL vs. Pre-op HL)), intra-operative reduced hip offset compared to pre-operative hip offset ($\Delta$(Reduced OS vs. Pre-op OS)), reduced hip length compared to contralateral hip length ($\Delta$(HL vs. opposite HL)) and reduced hip offset compared to contralateral hip offset ($\Delta$(OS vs. opposite OS)). These average values along with a value for one standard deviation from the average are shown in FIG. 5. The results show where there were differences in hip length or hip offset on opposite sides of the joint or between an intra-operative reduced joint and a pre-operative joint. Specifically, pre-operatively arthritic hips were on average 1.72 mm short and laterally subluxed 1.16 mm compared to the contralateral hip. The average change in hip length from pre- to post-implantation was 2.92 mm longer and the average change in offset was 1.77 mm shorter. Compared to the contralateral side, the hip operated upon was 1.20 mm longer and had a 0.61 mm shorter offset. Such results are indicative of the restoration of the hip anatomy.

Further comparisons were made based on the study data using the values obtained by the following equations:

$$\Delta[(\text{Reduced } HL + OS \text{ vs. pre-op } HL + OS)] =$$
$$\Delta(\text{Reduced } HL \text{ vs. Pre-op } HL) + \Delta(\text{Reduced } OS \text{ vs. Pre-op } OS)$$
$$\Delta[(\text{Reduced } HL + OS \text{ vs. opposite } HL + OS)] =$$
$$\Delta(\text{Reduced } HL \text{ vs. opposite } HL) + \Delta(\text{Reduced } OS \text{ vs. opposite } OS)$$

-continued
$$\text{Shuck Length Vector} = \sqrt{\Delta(\text{shuck test } HL \text{ vs. reduced } HL)^2 + \Delta(\text{shuck test } OS \text{ vs. reduced } OS)^2}$$

Reduced hip length and offset were compared to ipsilateral pre-operative values and intra-operative contralateral values per the equations above to determine $\Delta[(\text{Reduced HL+OS vs. pre-op HL+OS})]$ and $\Delta[(\text{Reduced HL+OS vs. opposite HL+OS})]$ for each patient in the study. And, through performance of the shuck test, shuck test hip length and shuck test offset were determined as shown in FIG. 3. Such shuck test values provided data for the determination of a shuck length vector for each patient as set forth in the shuck length vector equation. The results of these determinations were compared in various ways, including those illustrated in the charts of FIGS. 7-10. Of these results, only one patient with a shuck length vector having a magnitude over 25 mm exhibited a dislocation of the hip. The average magnitude of shuck length based on the study data was around 10 mm with a plus/minus one standard deviation range of approximately 5-15 mm.

Figure 7:
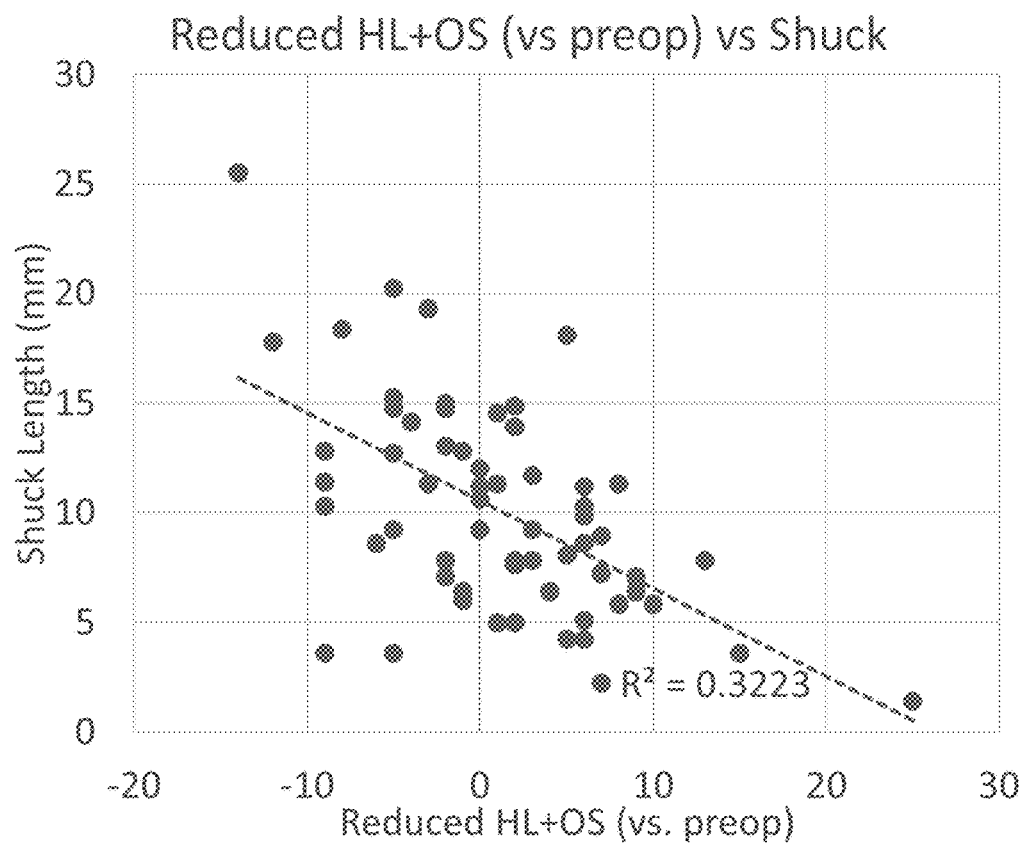
FIG. 7 is a chart comparing a delta between reduced and pre-operative hip length and hip offset information with shuck length for patients according to the study referenced in FIG. 4.

Delta values of reduced hip length and offset relative to pre-operative hip length and offset are compared to respective shuck length magnitudes for each patient in FIG. 7. This comparison is used to observe a relationship between tissue tension at reduction and changes in hip length and hip offset from pre-operative conditions to an intra-operative reduction condition. The results shown in FIG. 7 illustrate a meaningful inverse correlation between shuck length and the delta between reduced and pre-operative hip length and offset, with an $R^2$ value of 0.3223 for the fit of the linear regression shown on the chart relative to the patient data points. For the avoidance of ambiguity, it should be appreciated that $R^2$ equals a variance explained by the model (linear relationship on chart) over a total variance. The inverse correlation is generally expected for this comparison as a tighter joint should occur with larger increases in combined hip length and offset.

Figure 8:
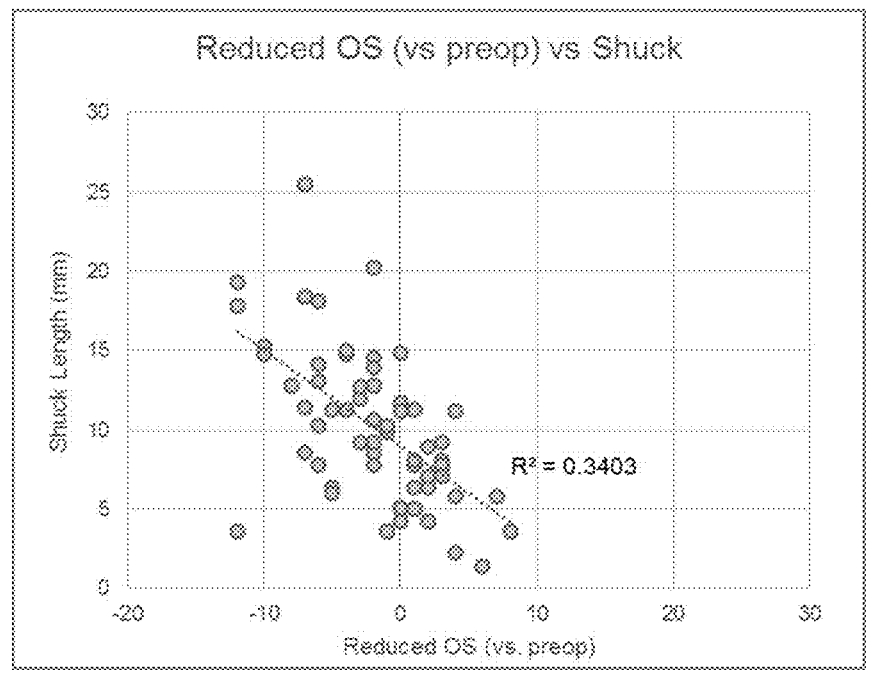
FIG. 8 is a chart comparing a delta between reduced and pre-operative hip offset information with shuck length for patients according to the study referenced in FIG. 4.
Figure 9:
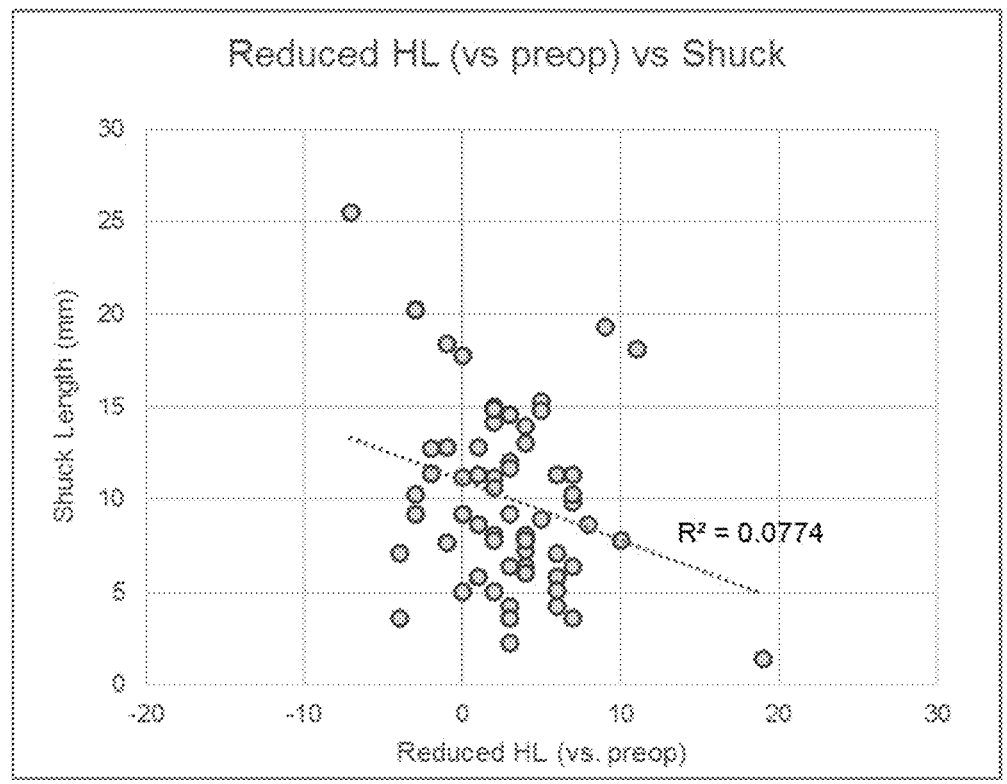
FIG. 9 is a chart comparing a delta between reduced and pre-operative hip length with shuck length for patients according to the study referenced in FIG. 4.
Figure 10:
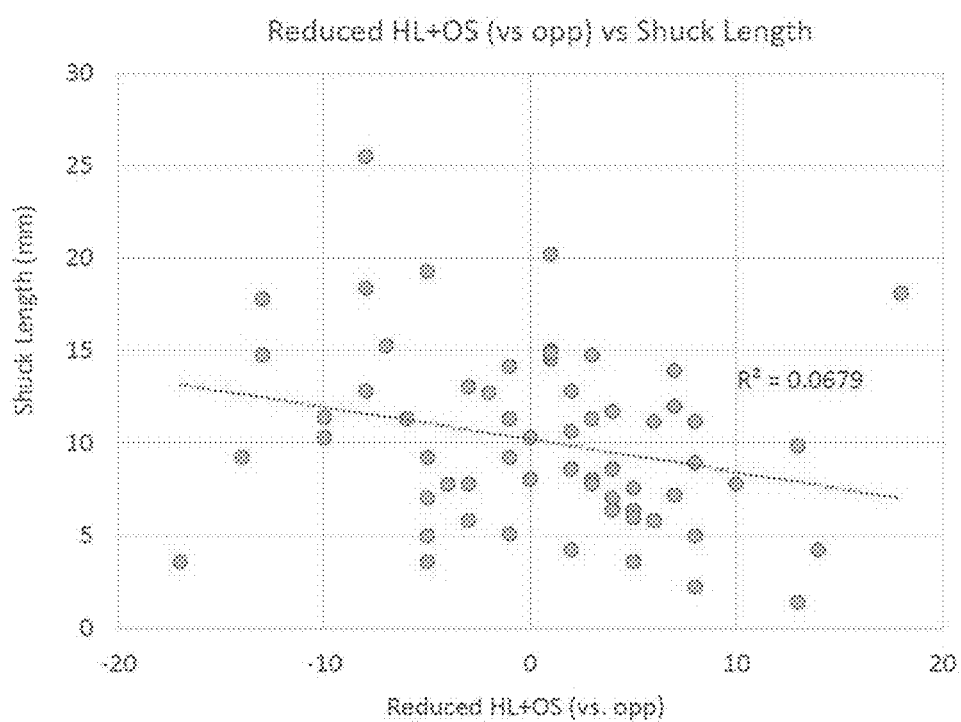
FIG. 10 is a chart comparing a delta of reduced hip length and offset between opposite joints with shuck length for patients according to the study referenced in FIG. 4.

In FIG. 8, delta values of reduced hip offset relative to pre-operative hip offset are compared to respective shuck length magnitudes for each patient. The linear regression for this relationship has a slightly stronger inverse correlation with the data points than that found in the relationship of the delta for hip length and offset between intra-operative and pre-operative with shuck length vectors as shown in FIG. 7, with an $R^2$ value of 0.3403. In FIG. 9, delta values of reduced hip length relative to pre-operative hip length are compared to respective shuck length magnitudes for each patient. The linear regression for this relationship has a relatively weaker inverse correlation with the data points than that for the hip offset, with an $R^2$ value of 0.0774. And, in FIG. 10, delta values of reduced hip length and offset relative to opposite (contralateral) hip length and offset are compared to respective shuck length magnitudes for each patient. This comparison is used to observe a relationship between tissue tension of a hip joint and differences between hip length and offset at reduction and in the contralateral hip joint. As with the delta values for hip length, the linear regression for this relationship has a weaker inverse correlation with the data points than the other comparative data, having an $R^2$ value of 0.0679.

Several other variables were analyzed for their effect on the shuck distance with no significant correlation found for gender difference, arthritis severity as classified by Tonnis grade, or femoral head size, e.g., 32 mm diameter vs 36 mm diameter.

Measurements related to the shuck test itself are summarized in FIG. 6. Here, averages and standard deviations of the hip length shuck distance and hip length offset distance for the patients in the study are provided. The mean hip length shuck distance was 7.17 mm and the mean offset shuck distance was 6.43 mm. And, an application of these values into the Pythagorean theorem gives a resultant shuck length vector magnitude of 10.07 mm at an angle of 41 degrees relative to a horizontal plane when the patient is in the lateral decubitus position. Thus, the shuck distance values shown in FIG. 6 are used to determine an average magnitude, i.e., length of the shuck length vector, and average direction of the shuck length vector, along with a respective standard deviation from the average.

Figure 11:
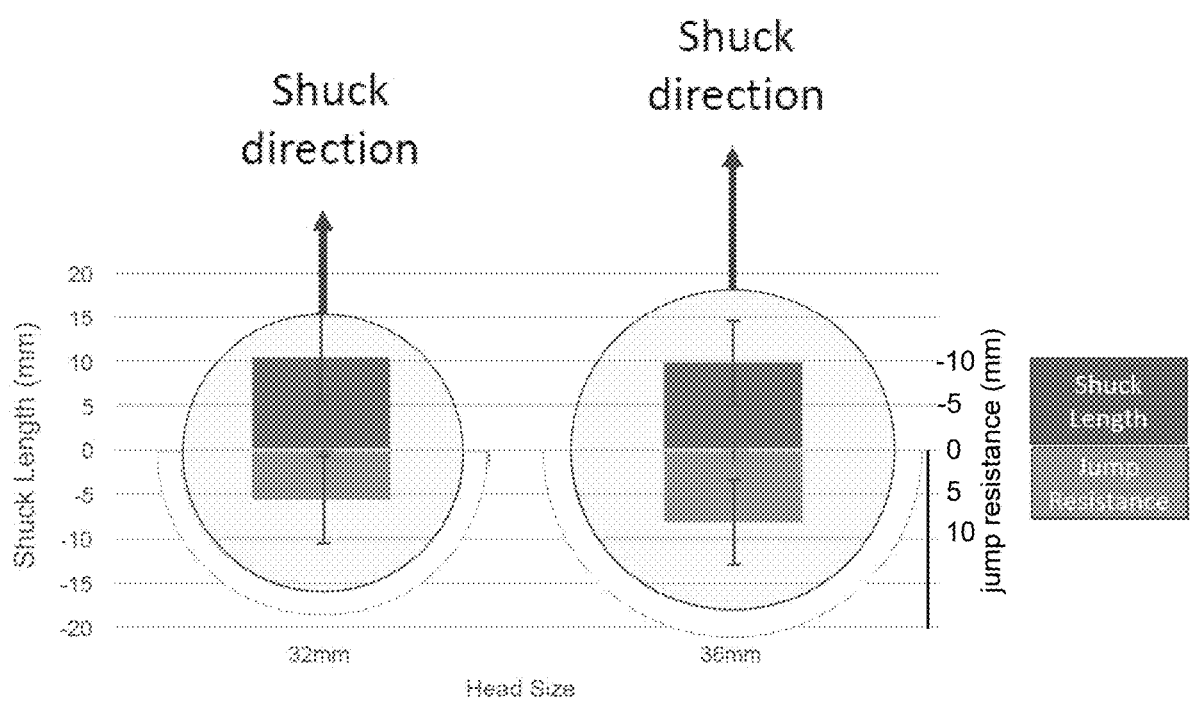
FIG. 11 is a chart illustrating jump resistance values for different femoral head sizes.
Figure 12:
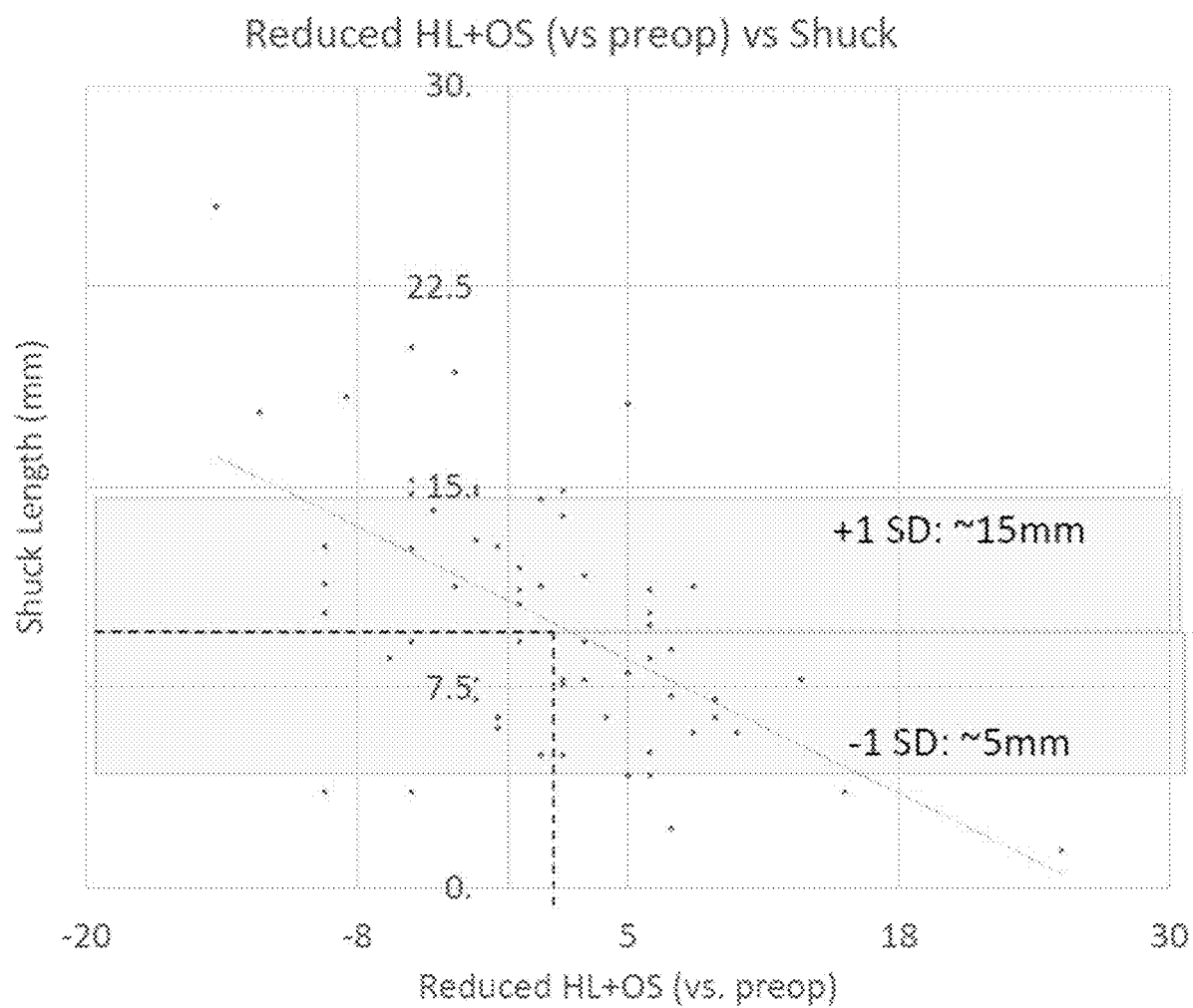
FIG. 12 is a chart showing a proposed safe range of shuck length magnitudes based on the study referenced in FIG. 4.

Further, the shuck length vector is also used to determine what is known as jump resistance. As described elsewhere in the disclosure, a jump resistance value is a magnitude of the shuck length vector subtracted from the femoral head radius. In specific examples derived from the study and shown in FIG. 11, an average shuck length vector was determined to be approximately 10 mm for an implant with a 32 mm femoral head diameter, thus yielding a jump resistance of 6 mm. And, an average shuck length vector was determined to be approximately 10 mm for an implant with a 36 mm femoral head diameter, yielding a jump resistance of 8 mm. These values suggest an acceptably low level of risk of dislocation in the joint. More generally, a jump resistance value greater than zero suggests a decreased risk of dislocation in the joint. Despite showing no significant difference in a magnitude of the shuck length vector between 32 and 36 mm diameter femoral heads, there is a greater jump resistance with the larger femoral heads.

Advantages of the described method are evidenced by the results of the study. The average magnitude of the shuck length vector is 10.1 mm with a standard deviation range of 5-15 mm, with 71% of the patients in the study falling into this range. All patients with significant hip length and offset changes, either greater than 15 mm in combined increase or greater than 10 mm in combined decrease, were outside of the 5-15 mm range. The data from the study showed that the average magnitude correlated to a slight increase in post-operative hip length and offset relative to pre-operative values. Thus, when a shuck test is performed as contemplated by the present disclosure, a magnitude of the determined shuck length vector should be compared against a safe zone of a specified or prescribed range of magnitudes, such as 5-15 mm in one example, to determine whether soft tissue tension is acceptable. Arriving at a result within the safe zone ensures joint stability without over or under tensioning the soft tissues. Additionally, a result in this range may be obtained with knowledge that hip biomechanics are restored through the surgical procedure. An additional assessment to confirm implant placement in the hip joint is possible through the determination of the jump resistance by verifying that the magnitude of the shuck length is less than a radius of the femoral head.

Other advantages are realized through the relationships evidenced by the study. These include that shuck length inversely correlates with increases in hip length and offset relative to the pre-operative condition of a patient. Increases in offset were shown to be a better predictor of reduced shuck length than hip length increases. Only a weak inverse correlation was observed between shuck length and hip length and offset discrepancies across opposite hips. While no change in shuck length was observed between 32 and 36 mm diameter femoral heads, 36 mm heads had a significantly larger jump resistance based on the shuck test due to the larger radius.

Although the disclosure herein has been described with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosure as defined by the appended claims.

The invention claimed is:

1. A method of evaluating soft tissue tension surrounding a hip of a patient when a femoral implant or a trial is disposed in a femur of the patient, the method using navigation and software to track positions of the femur and a pelvis of the patient in real time, the method comprising:
   intra-operatively reducing a femoral implant or a trial into an acetabulum of a patient;
   retrieving first coordinates of a femoral head center of the femoral implant or trial when the femoral implant or trial is in a reduced position;
   performing an intra-operative test to bring soft tissue of the patient into tension comprising:
      gripping a neck of the femoral implant or trial;
      holding and pulling the femur to distract the femur relative to the acetabulum; and
      pulling the neck to distract the femoral implant or trial from the acetabulum;
   retrieving second coordinates of the femoral head center when the femoral implant or trial is distracted from the acetabulum; and
   determining a distraction vector based on a difference between the first coordinates and the second coordinates in a coronal plane.

2. The method of claim 1, wherein determining the distraction vector further comprises:
   determining a hip offset vector based on a difference between the first coordinates and the second coordinates in the coronal plane along a medial-lateral direction;
   determining a hip length vector based on a difference between the first coordinates and the second coordinates in the coronal plane along a superior-inferior direction; and
   combining the hip offset vector and the hip length vector to obtain the distraction vector.

3. The method of claim 1, further comprising adjusting the reduced position of the femoral implant or trial or replacing the femoral implant or trial when the distraction vector has a magnitude outside of a prescribed range of distraction vector magnitudes, wherein magnitudes within the prescribed range of distraction vector magnitudes are indicative of soft tissue balance in the hip of the patient.

4. The method of claim 3, wherein the prescribed range of distraction vector magnitudes is from 5 mm to 15 mm.

5. The method of claim 1, further comprising replacing a first head of the femoral implant or trial with a second head larger than the first head when a jump resistance is less than zero, the jump resistance being a magnitude of the distraction vector subtracted from a radius of the first head.

6. The method of claim 1, further comprising, prior to retrieving the first coordinates:
   placing a fiducial marker on each of the pelvis and the femur;

collecting a first plurality of landmarks on the pelvis to register the first plurality of landmarks with a coordinate system; and collecting a second plurality of landmarks on the femoral implant or trial in the reduced position to register the second plurality of landmarks with the coordinate system, wherein the first coordinates and the second coordinates are derived from real-time coordinates of the second plurality of landmarks.

7. A method of evaluating soft tissue tension in a hip joint of a patient using navigation and software, the method comprising:

retrieving first head center coordinates of a center of a head of a femoral implant or a trial when the femoral implant or trial is reduced in an acetabulum of the patient;

capturing a real-time location of the head when the head is distracted from its reduced position during performance of an intraoperative test, the distraction of the head during the intraoperative test causing tension in soft tissue in the hip joint to increase relative to tension before distraction;

determining second head center coordinates of the center of the head while the head is distracted;

comparing the second head center coordinates to a peripheral tension-limit boundary of the center of the head, the peripheral tension-limit boundary being based on moving a femur holding the femoral implant or trial through a range of motion while distracted and defined by an outer limit of movement of the center of the head; and using a distraction vector defined by a difference between the first head center coordinates and the second head center coordinates to evaluate soft tissue tension when the distraction vector is aligned on an axis passing internal to the peripheral tension-limit boundary.

8. The method of claim 7, wherein the comparing step further comprises comparing the second head center coordinates to a boundary defined by a cone-shaped surface adjoining the peripheral tension-limit boundary with coordinates defining a center of the acetabulum.

9. The method of claim 7, wherein prior to using the distraction vector, the method further comprises:

determining a hip offset vector based on a difference between the first head center coordinates and the second head center coordinates in a coronal plane along a medial-lateral direction; and determining a hip length vector based on the difference between the first head center coordinates and the second head center coordinates in a coronal plane along a superior-inferior direction, wherein the distraction vector is a hypotenuse connecting the hip offset vector and the hip length vector.

10. The method of claim 9, further comprising adjusting the femoral implant or trial to change at least one of a reduction hip offset and a reduction hip length when the axis aligned through the distraction vector passes internal to the peripheral tension-limit boundary and a magnitude of the distraction vector is outside of a range from 5 mm to 15 mm.

11. The method of claim 7, further comprising repeating the intraoperative test when the axis aligned through the distraction vector passes on or external to the peripheral tension-limit boundary.

12. The method of claim 7, wherein performance of the intraoperative test involves:

gripping a neck of the femoral implant or trial;

holding and pulling the femur to distract the femur relative to the acetabulum; and laterally pulling the neck to distract the femoral implant or trial from the acetabulum.

13. A method of evaluating soft tissue tension surrounding a hip of a patient during an implant replacement procedure, the method using navigation and software to track positions of a femur and an acetabulum of the patient in real time, the method comprising:

dislocating the femur relative to the acetabulum;

retrieving first coordinates of a center of the acetabulum;

performing an intra-operative test to bring soft tissue of the patient into tension comprising holding and pulling the femur to distract the femur relative to the acetabulum;

retrieving second coordinates of a femoral head center of a femoral implant based on a position of the femoral implant when the femoral implant is disposed in the femur while the femur is distracted relative to the acetabulum; and determining a distraction vector based on a difference between the first coordinates and the second coordinates in a coronal plane.

14. The method of claim 13, further comprising, prior to retrieving the first coordinates:

placing a fiducial marker on each of the femur and a pelvis of the patient;

collecting a first plurality of landmarks on the pelvis to register the first plurality of landmarks with a coordinate system; and collecting a second plurality of landmarks on the femoral implant to register the second plurality of landmarks with the coordinate system, wherein the first coordinates and the second coordinates are derived from real-time coordinates of the second plurality of landmarks.

15. The method of claim 13, wherein performing the intra-operative test further comprises pulling the femur while monitoring a force associated with the pulling.

16. The method of claim 13, further comprising, prior to performing the intra-operative test, cutting a ligamentum teres of the patient to separate the femur and the acetabulum.

17. The method of claim 13, further comprising, prior to performing the intra-operative test, resecting a neck of the femur.

18. The method of claim 13, further comprising reducing the femoral implant in the acetabulum such that the first coordinates are retrieved when the femoral implant is reduced in the acetabulum.

19. The method of claim 18, further comprising displaying on a user interface the first coordinates, the second coordinates of the femoral head center and a real time distraction vector during performance of the intra-operative test.

20. The method of claim 13, wherein retrieving the second coordinates of the femoral head center further comprises retrieving third coordinates of a known location on the femur when the femur is distracted and determining the second coordinates based on a virtual location of the femoral head center relative to the third coordinates.

* * * * *